United States Patent [19]
Schuerch et al.

[11] Patent Number: 5,332,388
[45] Date of Patent: Jul. 26, 1994

[54] ULTRAVIOLET DISINFECTION MODULE

[75] Inventors: Peter Schuerch, Mechanicville; Richard K. Weltz, Richmond, both of Va.; Joseph E. Zuback, Camarillo, Calif.; Mervyn W. Bowen, Severna Park, Md.; James DiFalco, Irvington, N.Y.

[73] Assignee: Infilco Degremont, Inc., Richmond, Va.

[21] Appl. No.: 986,849

[22] Filed: Dec. 4, 1992

[51] Int. Cl.⁵ ............................ B08B 3/00; C02F 1/32
[52] U.S. Cl. .................................... 422/291; 422/24; 422/186.3; 250/436; 250/432 R; 250/431; 210/748; 134/104.1
[58] Field of Search ............. 422/24, 186.3, 291; 250/436, 432 R, 492.1, 431; 210/748; 134/104.1, 1

[56] References Cited

U.S. PATENT DOCUMENTS

| | | | |
|---|---|---|---|
| 3,138,708 | 6/1964 | Ellner et al. | 250/431 |
| 3,182,191 | 5/1965 | McFarland et al. | 250/435 |
| 3,456,107 | 7/1969 | Robertson | 250/431 |
| 3,462,597 | 8/1969 | Young | 250/431 |
| 3,562,520 | 2/1971 | Hippen | 250/372 |
| 3,566,105 | 2/1971 | Wiltrout | 250/435 |
| 3,634,025 | 1/1972 | Landry | 250/436 |
| 3,924,139 | 12/1975 | Hirose et al. | 250/527 |
| 4,017,734 | 4/1977 | Ross | 250/431 |
| 4,103,167 | 7/1978 | Ellner | 250/432 R |
| 4,358,204 | 11/1982 | Ellner | 366/118 |
| 4,367,410 | 1/1983 | Wood | 250/431 |
| 4,442,049 | 4/1984 | Bloomer | 261/148 |
| 4,482,809 | 11/1984 | Maarschalkerweerd | 250/436 |
| 4,619,050 | 10/1986 | Klemm | 34/4 |
| 4,728,368 | 3/1988 | Pedziwiatr | 210/748 |
| 4,757,205 | 7/1988 | Latel et al. | 250/435 |
| 4,767,932 | 8/1988 | Ellner | 250/435 |
| 4,899,056 | 2/1990 | Ellner | 250/436 |
| 5,006,244 | 4/1991 | Maarschalkerweerd | 210/243 |
| 5,019,256 | 5/1991 | Ifill et al. | 210/232 |
| 5,070,893 | 12/1991 | Dittrich et al. | 134/104.4 |
| 5,094,010 | 3/1992 | Jacobi et al. | 34/1 R |
| 5,103,847 | 4/1992 | Martin et al. | 134/157 |
| 5,114,685 | 5/1992 | Sapoff | 422/219 |

FOREIGN PATENT DOCUMENTS 1440077 6/1976 United Kingdom .
1602209 11/1981 United Kingdom .

Primary Examiner—Robert J. Warden
Assistant Examiner—Hien Tran
Attorney, Agent, or Firm—Miller & Christenbury

[57] ABSTRACT

An immersible and portable module for irradiating waste fluids and capable of in situ self cleaning including a first header capable of receiving and maintaining in position a multiplicity of ultraviolet light producing lamps.

The module includes a second header capable of receiving and maintaining in position said multiplicity of lamps and having an opening to receive cleaning fluids wherein the multiplicity of lamps are connected to the headers. The second header has a multiplicity of cleaning fluid exit holes proximate the lamps to permit the cleaning fluids to flow into the opening and outwardly from the holes and into contact with the lamps.

31 Claims, 9 Drawing Sheets

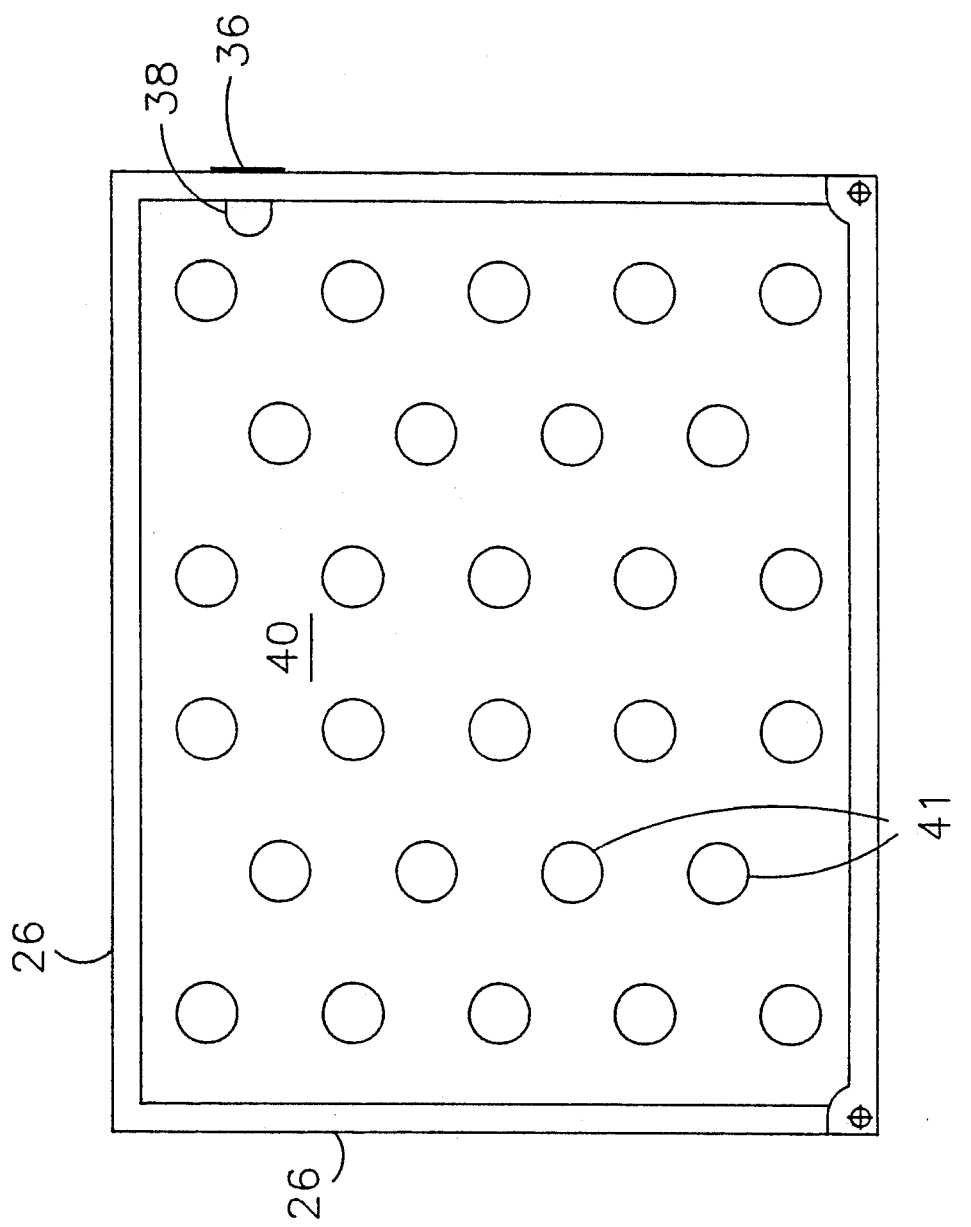

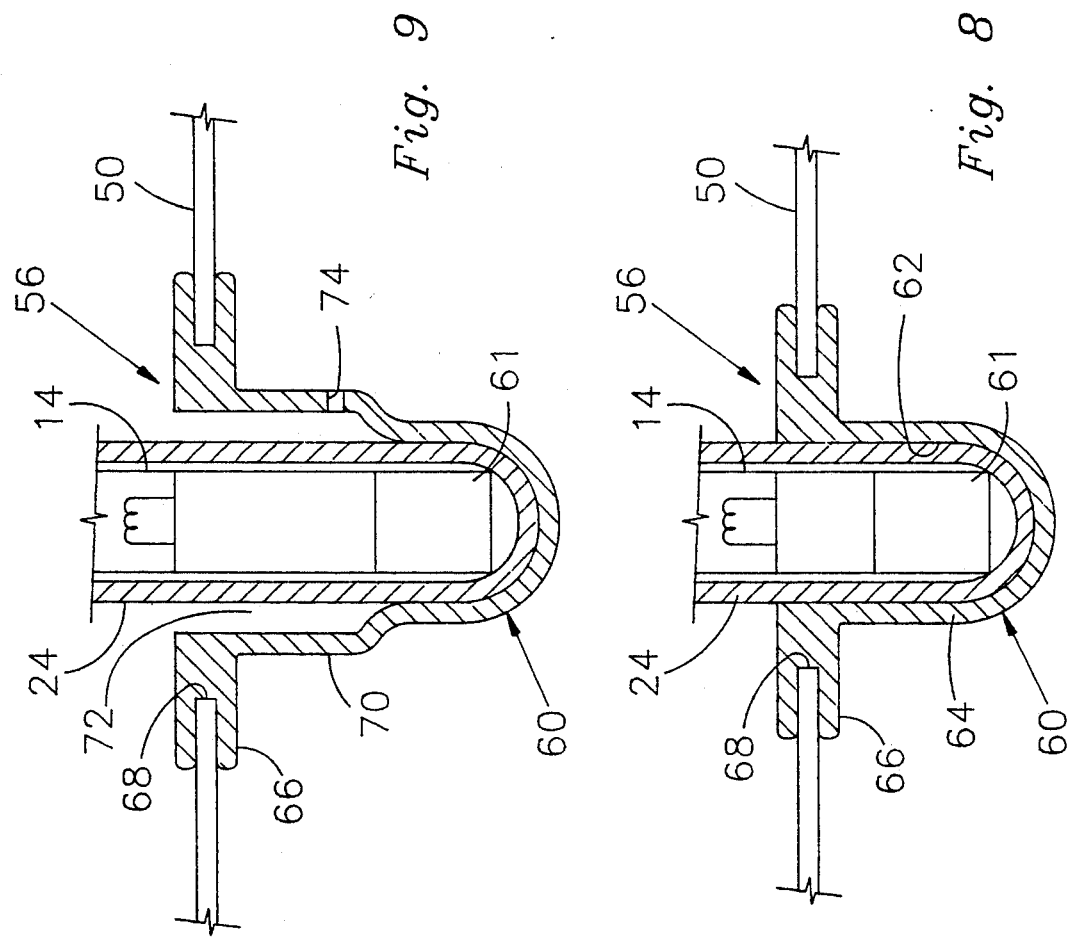

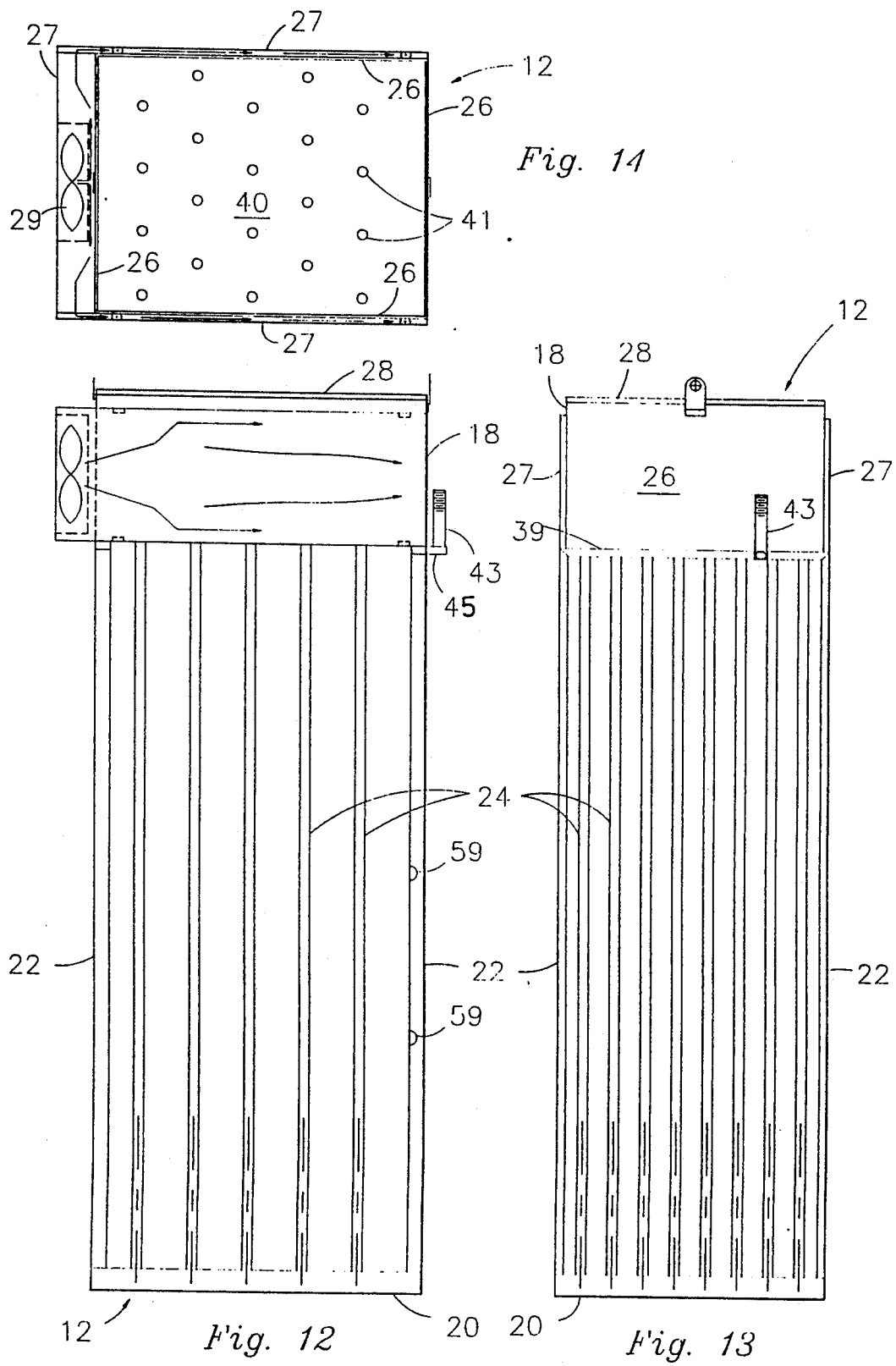

1

ULTRAVIOLET DISINFECTION MODULE

FIELD OF THE INVENTION

The invention relates to an ultraviolet disinfection module, particularly to an immersible, portable disinfection module capable of irradiating waste fluids and having in place self cleaning capabilities.

BACKGROUND OF THE INVENTION

The need to disinfect municipal and industrial waste water has gained increasing importance in view of increased environmental awareness and regulations mandating improved water quality. Such waste water has been disinfected with ultraviolet radiation in a number of methods and with a variety of apparatus. Such methodologies and apparatus typically include surrounding ultraviolet sources with protective jackets (hereinafter sometimes collectively referred to as "lamps") and submerging the lamps into the waste water as it flows through open or closed channels, open or closed containers or the like.

However, it has been a recurring and troubling problem that the transparent protective jackets surrounding the ultraviolet source become covered with particulate matter, residues, films and the like contained within the waste water over time. Of course, this covering builds up or increases in thickness over time and decreases the amount of ultraviolet light radiating outwardly from the lamps, thereby reducing the effective ultraviolet dose and decreasing disinfection efficiency. A number of attempts have been made to alleviate this problem. However, all attempts to date have resulted in apparatus which is either totally or partially ineffective, cumbersome to operate and maintain or economically prohibitive. For example, some apparatus utilizes structures that impedes the smooth flow of the waste water, requires additional power and personnel for operation, or causes the water to flow in patterns that reduce ultraviolet dosing efficiency.

Prior art known to the applicants includes U.S. Pat. Nos. 4,757,205, 4,899,056, 5,019,256 and 5,103,847. The most relevant of these patents utilize air to contact the transparent jackets to perform cleaning action. However, these systems involve the need to remove the transparent jackets and lamps from the waste water for treatment. Of course, this is a cumbersome process requiring periodic shut down of the system, extra operating personnel and equipment, and contributes to lowered efficiency of the entire system.

OBJECTS OF THE INVENTION

It is an object of the present invention to provide a disinfection apparatus capable of prolonging the period between cleaning and automatically cleaning itself.

It is another object of the invention to provide a disinfection apparatus capable of being cleaned while remaining in place, without removal from the disinfection pathway.

It is an important object of the invention to provide a portable disinfection apparatus which contains in one structure the capability to both disinfect water and clean itself.

Other objects and advantages of the invention will become apparent to those skilled in the art from the drawings, the detailed description of detailed embodiments, and the appended Claims.

SUMMARY OF THE INVENTION

The present invention provides a novel apparatus for irradiating and disinfecting waste fluids which is compact and portable and is also capable of in place self-cleaning. The device consists of a module having an upper header capable of receiving a multiplicity of ultraviolet producing lamps and a lower header capable of receiving cleaning fluids, which may be liquids or gases, together with the ultraviolet light lamps. The module further contains a means capable of transporting the cleaning fluids to the lower header. The lower header has a multiplicity of cleaning fluid exit holes proximate the lamps to permit the cleaning fluids to flow outwardly from the lower header, into the waste water strew, and into contact with the lamps.

BRIEF DESCRIPTION OF THE DRAWINGS

FIG. 4 is a schematic top plan view of the modules shown in FIGS. 2 and 3, prior to installation of lamps and jackets, with the top cover removed for ease of understanding.

FIG. 8 shows a schematic front elevational cross section of a lamp and jacket positioned in one embodiment of a grommet located in the lower header shown in FIGS. 6 and 7.

FIG. 9 shows a schematic front elevational cross section of another embodiment of the grommet shown in FIG. 8.

FIG. 12 shows a front elevational view of another embodiment of a module of the invention.

FIG. 13 shows a side elevational view of the module shown in FIG. 12.

FIG. 14 shows a top plan view of the module shown in FIGS. 12 and 13 without a top cover, for ease of understanding.

DETAILED DESCRIPTION OF THE INVENTION

Figure 1:
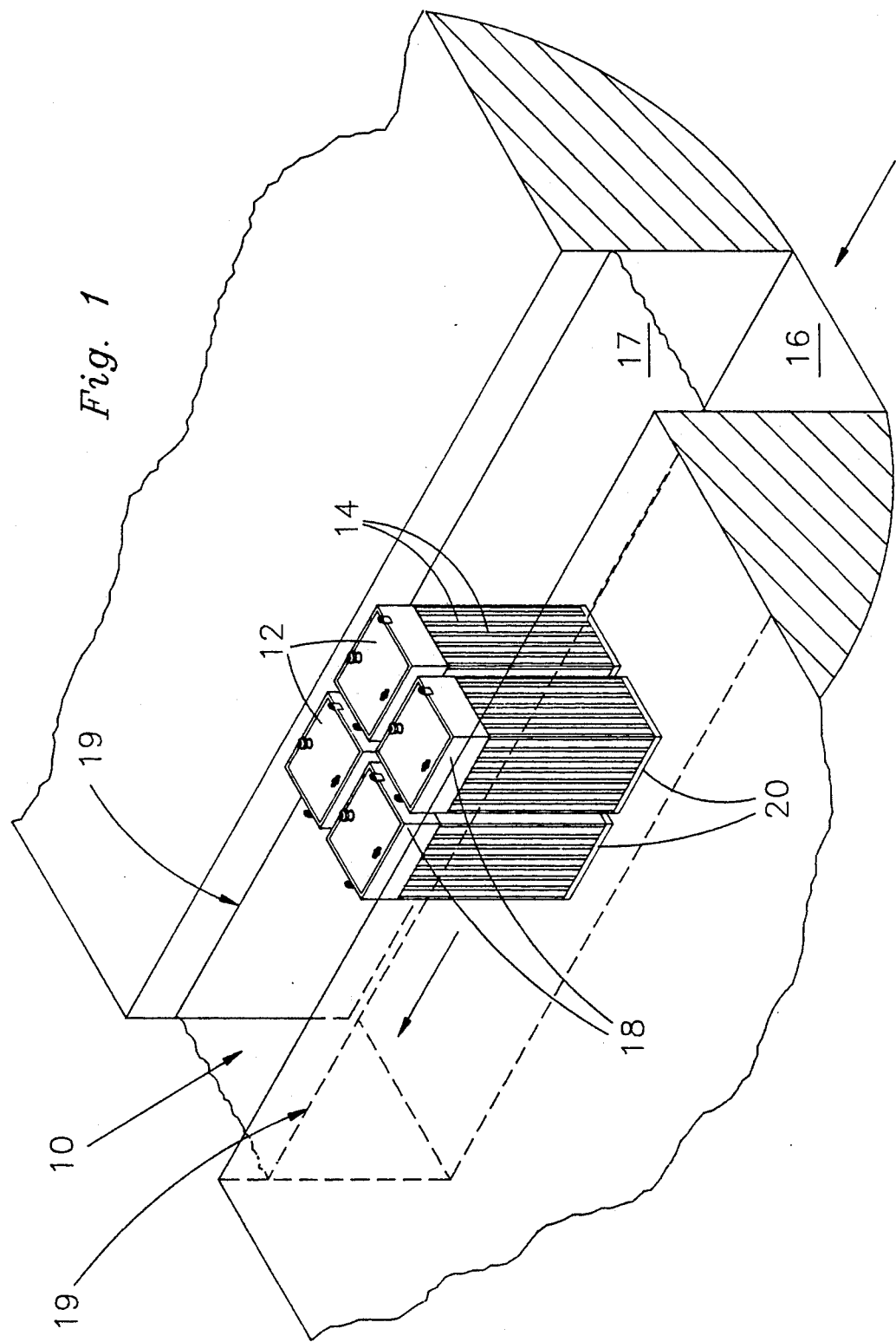
FIG. 1 shows a schematic perspective view of portable and immersible modules of the invention located in a portion of an open channel in accordance with preferred aspects of the invention.

It will be appreciated that the following description is intended to refer to the specific embodiments of the invention selected for illustration in the drawings and is not intended to define or limit the invention other than in the appended Claims.

Turning now to the drawings in general and FIG. 1 in particular, the number 10 designates an open channel through which waste water flows for disinfection treatment. One or more immersible and portable disinfection modules 12 are located in channel 10 to irradiate waste water with ultraviolet and thereby disinfect it as it flows through channel 10. Each module includes a multiplicity of lamps 14 in transparent jackets 24 (see also FIG. 3) located between upper header 18 and lower header 20 which in the embodiment shown are vertically oriented in prearranged patterns to evenly and completely irradiate with a prescribed dose of ultraviolet and disinfect all waste water as it passes through the channel. The modules rest on the floor 16 of channel 10 and are positioned adjacent to walls 17.

Channel 10 is sized so that waste water passes lamps 14 in transparent jackets 24 and is maintained at a predetermined depth which preferably remains at or below water surface 19, which is below upper header 18. The quantity, flow rate, type and composition of the waste water is affected by other systems and apparatus known in the art and not discussed herein.

Figures 2, 5:
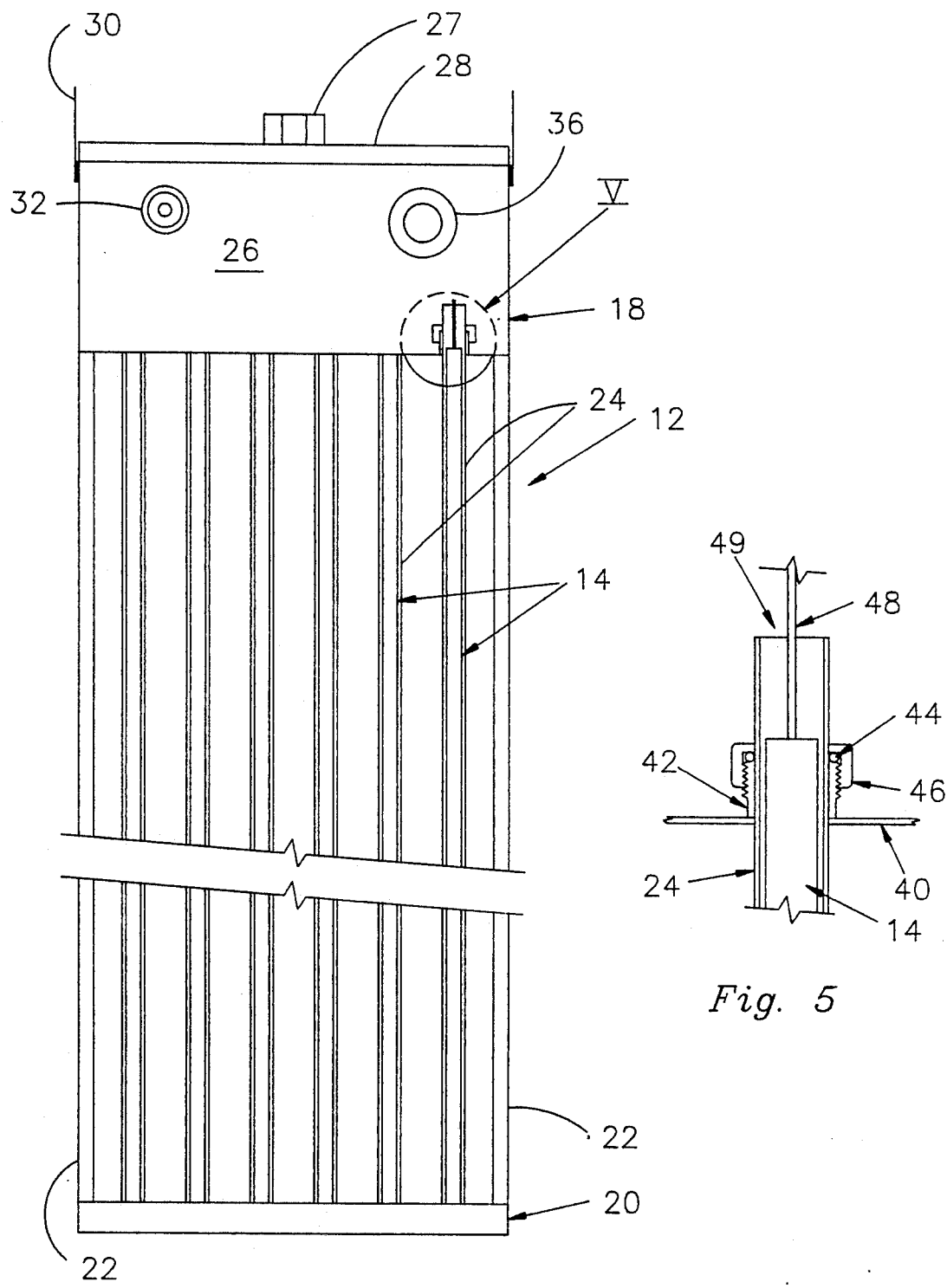
FIG. 2 shows a front elevational view of a module of the invention.
FIG. 5 is an exploded front elevational cross section taken from FIG. 2 of a lamp and its surrounding protective jacket extending through and connected to a module upper header.
Figure 3:
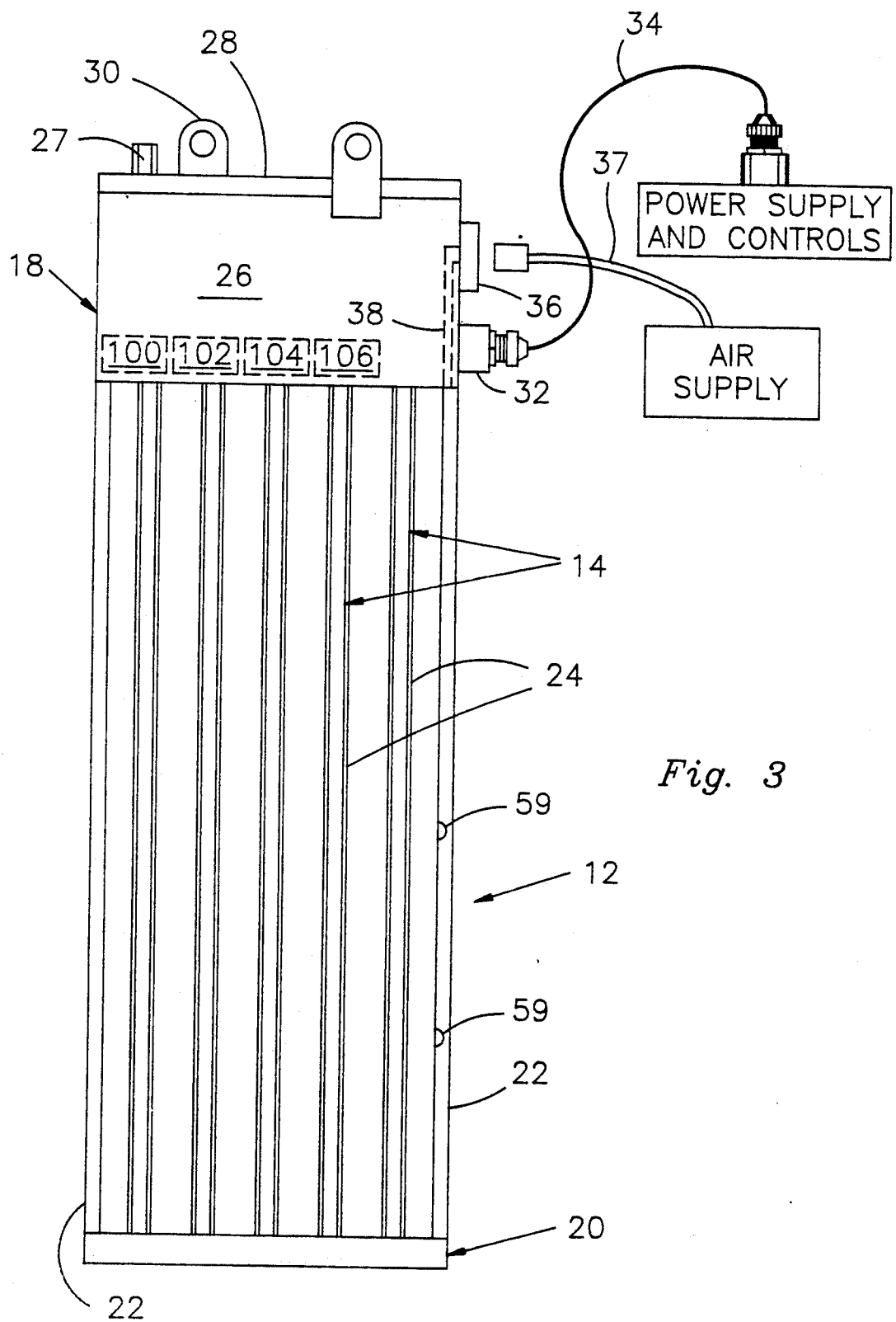
FIG. 3 shows a side elevational view of the module shown in FIG. 2.

FIGS. 2 and 3 show one embodiment of a module 12 in accordance with the invention. The integral structure of module 12 includes an upper header 18 and a lower header 20. Legs 22 connect upper and lower headers 18 and 20 and are preferably spaced apart at the respective corners of module 12. Leg 22 on the right hand side of FIG. 3 contains tubular exit holes 59 which are located about one-half and one-quarter, respectively, of the distance from lower header 20 to upper header 18. A multiplicity of transparent jackets 24 are connected between upper and lower headers 18 and 22 and each jacket 24 contains one or more lamps 14.

Upper header 18 includes side walls 26 and a removable cover 28. Cover 28 may be hinged or otherwise connectable to upper header 18 and is most preferably sealable to protect against water leakage. Handle 27 connects to cover 28 and insures that cover 28 remains in a closed position during module operation. Raising and lowering eyes 30 are connected to side walls 26 for ease of location and are used to move module 12 into and out of channel 10.

Module 12 is equipped with electrical connector 32 on one of side walls 26 which permits multiconductive cable 34 to connect between lamps 14 and various power and control devices. Side wall 26 also includes air supply connector 36 to introduce air, which is the especially preferred fluid, for jacket cleaning, into module 12. Air supply connector 36 in side wall 26 leads to air supply pipe 38, which is preferably located interiorly of upper header 18, and in one embodiment in turn connects to at least one of legs 22, which is hollow, and channels air to lower header 20. Air supply connector 36 is dimensioned to receive air supply hose 37, which connects to an air supply.

FIG. 4 shows the interior, in a schematic top plan view, of upper header 18. It should be understood that upper header 18 contains wiring associated with lamps 14, electronic lamp controllers 100, and/or ballasts 102, lamp monitor 104, data collector 106 and a number of devices not shown herein that contribute to the operation of the system and the module. Such devices include connecting wires, coolant devices such as fans, blowers and the like, as well as alarms, readouts, microprocessors, etc. The need or desirability of these items is influenced by the particular characteristics of each treatment facility.

Side walls 26 of upper header 18 form a rectangle around upper header floor 40. One side wall 26 includes access for air supply connector 36, which connects to air supply pipe 38. Upper header floor 40 contains a multiplicity of jacket receiving openings 41, which are provided with threaded collars 42 (see FIG. 5).

FIG. 5 shows an exploded view of the connection of a jacket 24, having an interiorly positioned lamp 14, with upper header floor 40. Upper header floor 40 includes a threaded collar 42 which is typically connected by welding. Jacket 24 extends upwardly through threaded collar 42 and is sized to be slightly smaller in outer diameter than the inner diameter of collar 42. An o-ring 44 is located at the topmost edge of threaded collar 42 and positioned around jacket 24. The inner diameter of o-ring 44 is preferably slightly smaller than the outer diameter of jacket 24 to provide a water tight seal. Nut 46 threadingly engages the threads of threaded collar 42 and compresses o-ring 44 to cause a watertight seal between jacket 24 and threaded collar 42. Such a seal prevents ingress of water into upper header 18 which could damage the wiring, lamps 14 or other devices located interiorly of upper header 18.

Lamp 14 is located interiorly of jacket 24 and has a wire 48 extending upwardly into upper header 18 which connects to appropriate power supply and control devices. The top opening 49 of jacket 24 need not be closed or sealed. Use of rubberlike o-ring 44 also provides a comparatively soft cushion for jacket 24, which is most preferably made from quartz glass, and may be susceptible to cracking and breaking during shipment or module placement in channel 10 or upon subsequent movement of module 12.

Figure 6:
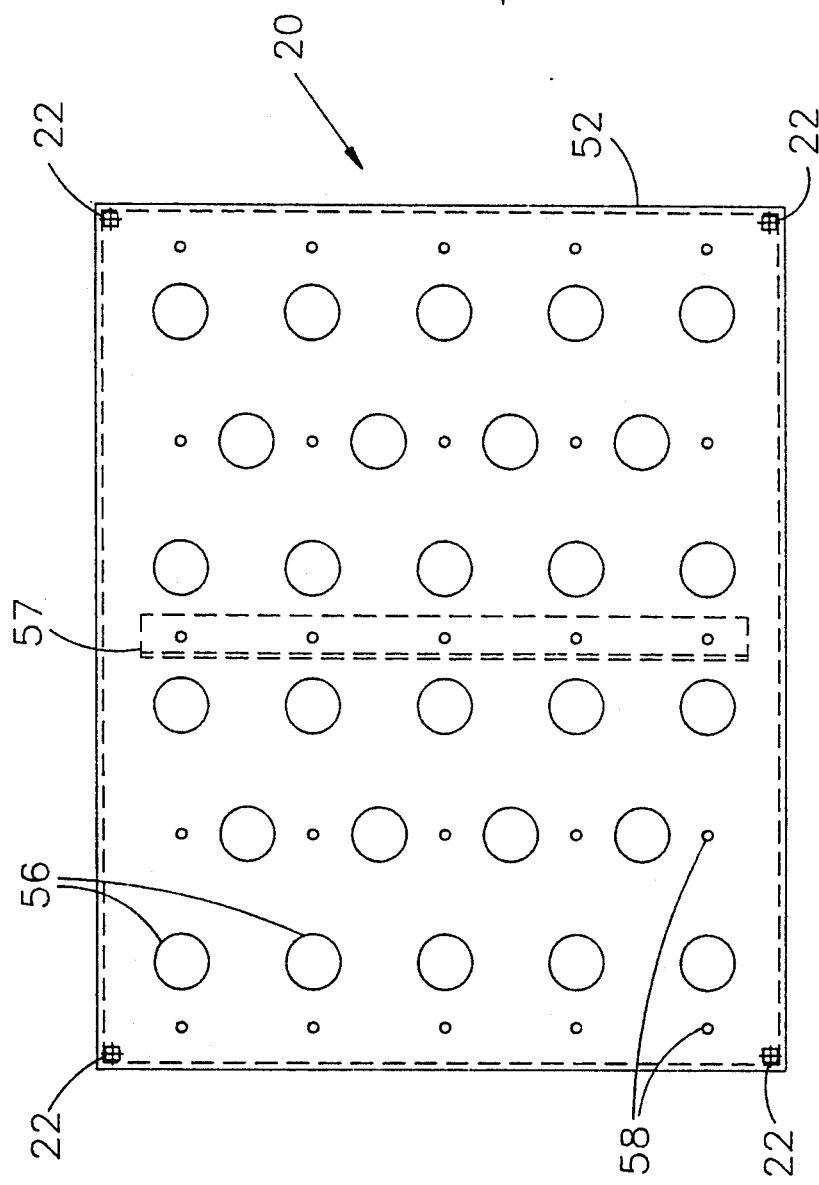
FIG. 6 shows a top plan view of a bottom header, prior to installation of lamps and jackets, in accordance with the invention.
Figure 7:
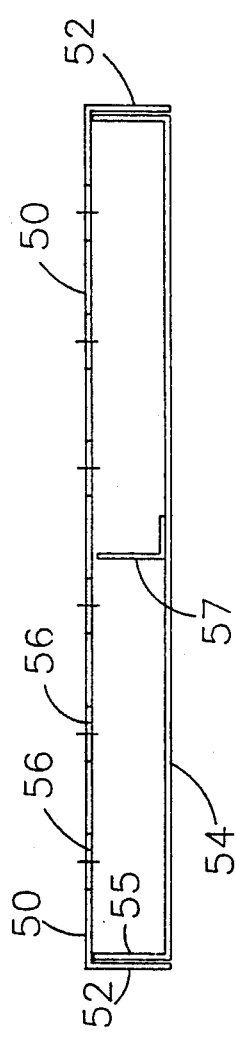
FIG. 7 shows a front elevational cross section of the bottom header shown in FIG. 6.

FIGS. 6 and 7 show a preferred embodiment of lower header 20. Lower header 20 connects to upper header 18 by legs 22, preferably located in the respective corners. At least one leg 22 is hollow and fluid tight to receive air from air supply pipe 38 located in upper header 18. In the preferred embodiment lower header 20 consists of top pan 50, outer side walls 52, floor 54 (which may be omitted in certain applications) and inner side walls 55. Top pan 50 contains a multiplicity of jacket receiving openings 56, the number and positioning of jacket receiving openings 56 corresponding to the number and positioning of threaded collar openings 42 in upper header 18 (see FIGS. 4 and 5). Bracket 57 is positioned between top pan 50 and floor 54 to serve as a reinforcing member for lower header 20.

Top pan 50 also includes a multiplicity of exit holes 58 which permit air to flow outwardly of lower header 20 through top pan 50 and into contact with jackets 24 to allow self-cleaning of jackets 24.

FIG. 8 shows one embodiment of a grommet 60 located in a jacket receiving opening 56 in top pan 50. Grommet 60 is preferably shaped to receive the "test tube" shaped end of jacket 24. Accordingly, the interior surface 62 of body portion 64 is preferably similarly shaped to the "test tube" shape of the bottom of jacket 24 and at least a portion of the body portion 64 is constructed to have an inner diameter substantially the same as or smaller than an outer diameter of the lamp 14. Grommet lips 66 closely engage the top and bottom surfaces of top pan 50 by way of a slot 68 which is sized substantially the same as or slightly smaller than the thickness of top pan 50. This creates a water tight seal between grommet 60 and jacket receiving opening 56 to prevent unwanted escape of air from lower header 20.

The bottom end of lamp 14 rests on a resilient spacer 61 which is positioned at the bottom of jacket 24.

FIG. 9 shows another embodiment of grommet 60 which is similar to grommet 60 of FIG. 8 in many respects. However, grommet 60 of FIG. 9 includes an additional widened sleeve portion 70 which creates an annular space 72 between sleeve portion 70 and jacket 24. Also, sleeve 70 has one or more openings 74 to permit passage of air from the interior of lower header 20 into annular space 72 and into contact with jacket 24 to act as a cleaning agent. This can eliminate the need for holes 58 shown in FIG. 6. The bottom end of lamp 14 rests on a resilient spacer 61 which is positioned at the bottom of jacket 24.

Figure 10:
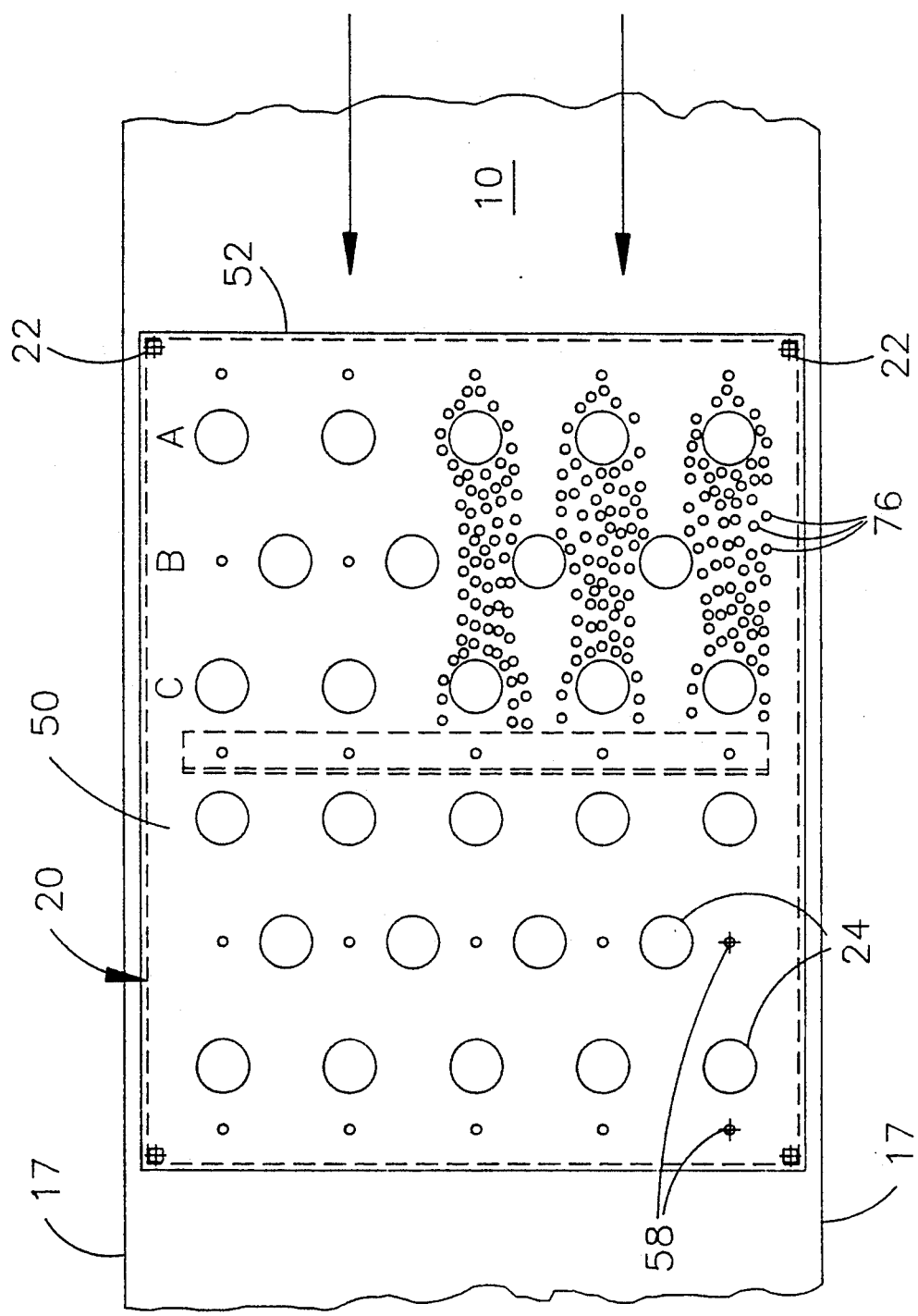
FIG. 10 shows a schematic top plan view of the lower half of a module of the invention located in a waste water disinfection channel and illustrating cleaning of jackets with cleaning fluid.

FIG. 10 shows the lower portion of the module of FIG. 6 placed within a channel 10 for the disinfection of waste water. In this particular embodiment, one module is sufficient to disinfect the waste water stream flowing through channel 10, although at least two modules are typically employed even if one will provide the needed disinfection. The module is slightly spaced away from walls 17 and lies directly in the path of a stream of waste water which is flowing in the direction shown by the two arrows. Bubbles 76 are streaming outwardly from exit holes 58 in top pan 50. Bubbles 76 are shown impacting against jacket 24 to act as a cleaning agent.

Figure 11:
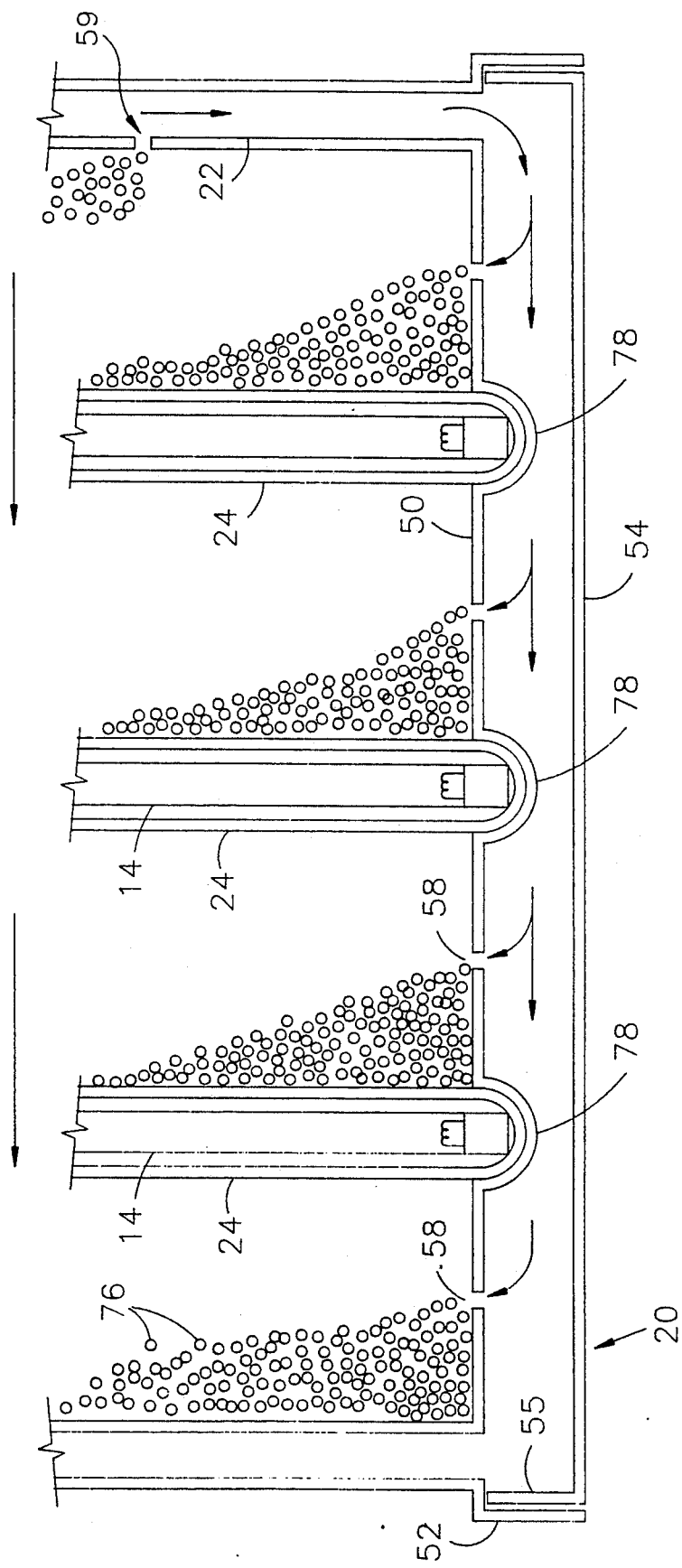
FIG. 11 shows a schematic side elevational view of a module of the invention and illustrating cleaning of jackets with cleaning fluid.

FIG. 11 shows the lower portion of another embodiment of module 12 wherein jackets 24 are positioned in indentations 78 in top pan 50. Bubbles 76 are streaming outwardly of exit holes 58 and into contact with jacket 24. Waste water is flowing in the direction of the arrows at the top of FIG. 11.

FIGS. 12-14 show an alternate, preferred embodiment of module 12. Upper header 18 is connected to lower header 20 by way of legs 22. Jackets 24 are positioned between and connected to upper header 18 and lower header 20. Upper header 18 consists of four side walls 26, header floor 40 having a multiplicity of jacket receiving openings 41, and a cover 28. Upper header 18 is preferably tack welded to a pair of horizontal air supply lines 39, which connect to legs 22.

Three of the four side walls 26 are surrounded by a shroud 27 which creates an open space around a large portion of upper header 18. Fan 29 is located between one side wall 26 and a portion of the shroud 27. Fan 29 is operable to circulate ambient temperature air within shroud 27 around side walls 26 as shown by the arrows in FIGS. 12 and 14.

Both legs 22 on the upstream side of module 12, as shown in FIG. 13, connect to air supply line 38. Air supply line 38 connects to a similarly horizontally air fluid supply inlet 45 which in turn connects to a vertically oriented air nipple 43.

Operation of the system of the invention will now be described below in connection with all of the drawings.

The number and configuration of modules necessary to disinfect a given waste water stream flowing through channel 10 is calculated by methodology well known in the art and not discussed herein. The proper number of modules are then positioned within channel 10 to ensure that an effective dose of ultraviolet is administered to the waste water as it flows. Modules 12 may be employed singly, in rows across channel 10, in banks of modules downstream from one another or in other arrangements known in the art.

Over the course of time, particulates carried by the waste water accumulate on jackets 24 to form a film, thereby causing the need for cleaning. Such cleaning can be achieved by utilizing the effects of a scrubbing fluid contacting the jackets 24 on an as needed periodic basis or on a continuous basis if desired. The invention provides an effective means of accomplishing this task without stopping the flow of waste water and/or without removing the modules. Initiation of the cleaning function may be performed automatically on a predetermined basis or manually, depending on the sophistication and capability of control devices selected. While any number of cleaning fluids, either liquid or gaseous, may be used, air has been found to be an efficient cleaning fluid.

Air is pumped from an air supply through air supply connector 36 and into air supply pipe 38, located interiorly of upper header 18 as shown in FIG. 3. However, it is possible in alternative constructions for the air supply to avoid upper header 18 and connect directly into or onto leg 22 if desired. Air supply pipe 38 connects to at least one of legs 22, which is hollow. Air then flows downwardly through leg 22 and into lower header 20 wherein it accumulates beneath top pan 50. Exit holes 58 permit air to bubble outwardly from lower header 20 in a predetermined configuration to maximize contact of the air bubbles with the jackets 24. Of course, it is possible to vary the rate of air introduction into module 12 to further facilitate cleaning action of the air bubbles against jackets 24. Also, grommet 60 of FIG. 9 may be employed in addition to or in place of exit holes 58 to achieve excellent bubble/jacket cleaning contact through the effect of bubbles emanating from openings 74.

Patterns of cleaning action of the bubbles 76 are shown in FIGS. 10 and 11 and it is important that the patterns be designed to maximize air bubbles 76/jacket 24 contact. FIG. 11 shows bubbles 76 moving outwardly of lower header 20 through exit holes 58 in top pan 50, upwardly toward water surface 19 (see FIG. 1) and into contact with jackets 24. A continuous flow of bubbles 76 moves upwardly and contacts substantially the entire length of jackets 24.

FIG. 10 shows the same cleaning phenomenon from a top plan view wherein a module is positioned between two channel walls 17 in channel 10. Bubbles 76 contact the first row "A" of jackets 24 on their right hand faces in the figure and as the flow of water moves toward the left in the direction of the arrows, the bubbles flow against the jackets and split into two streams, one stream flowing against each side of each jacket 24. The bubbles move along the surface of the jackets and with the flow of water until encountering the next row of lamps labelled "B" and contacts the jackets 24 in row "B". The bubbles then travel along and in contact with the jackets 24 toward the left in the direction of the arrows toward row "C" wherein the bubbles continue further cleaning action. This phenomenon continues until the bubbles flow beyond the last row of jackets 24 on the left hand side of the figure. Of course, reversing the flow of fluid in channel 10 would cause an opposite effect wherein bubbles would initially contact opposite faces of jackets 24 to initiate cleaning from the other left hand side.

It is important to note that FIGS. 10 and 11 are basic representations of the bubble flow patterns that actually occur. Actual bubble flow may be altered by a number of factors such as air quantity introduced, exit hole 58 or openings 74 size, waste water composition and flow rate, the number and size of modules, width and depth of channel 10 and the like.

It is also important that cleaning take place and be effective from top pan 50 upwardly to the surface of the water flow (water surface 19) to maximize disinfection efficiency and that the water not be subjected to directional forces while flowing that could lead to uneven ultraviolet irradiation. This has been a serious problem in prior systems that fail to achieve this important task.

The embodiment of the invention of module 12 shown in FIG. 12 provides additional cleaning capability by providing cleaning fluid exit holes 59 at positions well above lower header 20 and the fluid cleaning exit holes 58 located at lower header 20. Fluid cleaning exit holes 59 are preferably located between about one-quarter and three-quarters of the distance from lower head 20 to upper header 18, although locations at one-half the distance and at one-quarter of the distance are especially preferred. It should be noted that there is no requirement that the fluid cleaning exit holes 59 be located in the same legs 22 that receive fluid from a horizontal air supply line 39, so long as they are located upstream of the direction of the travel of waste water in channel 10. Utilization of the preferred embodiment shown in FIG. 12 on a daily basis for as few as ten minutes per day is capable of reducing cleaning requirements by four to six orders of magnitude.

The configuration and placement of modules 12 within the channel causes lower header 20 to be the effective floor of channel 10. This is important in insuring that complete irradiation of the waste water be achieved. As shown in FIGS. 8, 9 and 11, the construction of the lower portion of module 12 surrounding lower header 20 permits water to flow through channel 10, above top pan 50, in a relatively undisturbed pattern which facilitates complete irradiation of the waste water as it passes by module 12. Spacer 61 is sized to ensure that the filaments of lamps 14 are most preferably located at the top of grommet 56 to obtain optimal dosages. Spacer 61 is preferably made from an inert but resilient material to protect jacket 24 from shock or breakage during lamp installation or module movement.

Legs 22 are sized and located to virtually eliminate blockage of irradiating ultraviolet and upper header 18 is most preferably totally removed from the water to eliminate obstruction of ultraviolet near the top of the water flow. The construction of the invention minimizes and substantially eliminates water passing module(s) 12 without being exposed to the minimum required dosage of ultraviolet radiation.

Prior art systems have typically contained structure that results in obstructions causing uneven irradiation or blind spots as the waste water passes the lamps. Of course, this is highly undesirable as it results in less than complete application of ultraviolet dosages.

It is also an advantageous feature of the invention, as illustrated in FIG. 11, that the placement of the bottom portion of lamps 14 within jackets 24 permits the lowermost portion of lamps 14 to provide ultraviolet coverage along top pan 50, whereas prior art systems typically do not provide structure permitting adequate irradiation of the lowermost portion of the channel. By use of either grommets 60, holes in top pan 50 or test tube shaped indentations 78 in top pan 50, the electrodes of lamps 14 are sufficiently recessed so that ultraviolet radiation projecting outwardly from the lights fully covers the waste water flowing past the lamps. Also, the special design of grommets 60, which do not extend upwardly from top pan 50, avoids the usual undesirable uneven water flow patterns that can result in ineffective irradiation doses. Further, the flexibility of the grommets 60 permits tightening of units 46 in upper header 18 without having exact vertical orientation of jackets 24.

Although this invention has been described in connection with specific forms thereof, it will be appreciated that a wide variety of equivalents may be substituted for the specific elements described herein without departing from the spirit and scope of this invention as described in the appended Claims. For example, the upper and lower headers 18 and 20 need not be totally vertically aligned so that the lamps are perpendicular to the headers. The upper and lower headers 18 and 20 can be arranged so that the lamps are aligned out of vertical. The lamps may extend between the headers at various angles to vertical, including horizontal.

It is also possible to employ module 12 without floor 54 and inner side walls 55 of lower header 20. The integral construction of top pan 50 and outer side walls 52 permits air to reside interiorly of lower header 20 without escaping prior to exiting from exit holes 58. Floor 54 can also be used in a removable configuration which permits easy access to exit holes 58 from both sides of top pan 50 but helps to prevent collection of suspended solid around lower header 20.

Still another advantageous feature of one especially preferred embodiment of the invention resides in the self cooling ability of the module by virtue of cooling shroud 27. Of course, upper header 18 is typically filled with a variety of electronic apparatus such as ballasts, electronic lamp controllers, data control assemblies, lamp control assemblies and the like, some or all of which generate heat. Excessive heat generation can over time cause detrimental effects to the electric and electronic components contained within upper header 18. Accordingly, it is important to provide an effective means to cool those components. Cooling shroud 27 and fan 29 permits three sides of header 18 to be cooled by free circulation of air about side walls 26. In this way, heat generated by the electric and electronic components in upper header 18 may be effectively dissipated.

Modules 12 may be connected to various types of power and control devices. The power supply is typically found at the site and is preferably a standard commercial building type, although modules 12 may be connected to alternate supplies such as generators and the like. Modules 12 are preferably connected to function control devices that coordinate operation of the entire disinfection system. One particular control function allows modules 12 to automatically, either continuously or periodically, initiate or terminate cleaning by operating a time device, water flow rates, quantities and the like, the air supply and an alarm system, for example. The control devices can also be capable of changing or adding to cleaning fluids if a multiple fluid supply is desired.

Modules 12 are most preferably constructed from stainless steel and welded together, although other materials and assembly methods may be substituted or added.

What is claimed is:

1. An immersible and portable module for irradiating fluids and capable of in situ self cleaning comprising:
   a multiplicity of ultraviolet light producing lamps;
   a first header for receiving and maintaining in position said multiplicity of ultraviolet light producing lamps; and a second header for receiving and maintaining in position said multiplicity of lamps and having an opening to receive cleaning fluids, said multiplicity of lamps being positioned between said headers;

said second header having a multiplicity of cleaning fluid exit holes proximate said lamps to permit said cleaning fluids to flow into said opening and outwardly from said holes and into contact with said lamps.

2. The module defined in claim 1 wherein the second header has a first side and a second side located opposite said first side, said lamps being positioned between said first and second sides, and at least some of said cleaning fluid exit holes are located between said first side and said lamps.

3. The module defined in claim 1 wherein said lamps are positioned interiorly of ultraviolet transmissive jackets, each lamp being electrically connected to a power source.

4. The module defined in claim 1 further comprising a support member connected between said headers.

5. The module defined in claim 4 wherein said support member is hollow and transports said cleaning fluids therethrough.

6. The module defined in claim 4 further comprising additional support members spaced apart from said support member and from one another and connected between said headers.

7. The module defined in claim 6 wherein at least one of said support member and said additional support members contains at least one supplemental cleaning fluid exit hole at position spaced from said second header.

8. The module defined in claim 7 wherein said at least one supplemental cleaning fluid exit hole is located between about one-quarter to about three-quarters of the distance between said headers from said second head.

9. The module defined in claim 7 wherein said at least one supplemental cleaning fluid exit hole is located about half way between said headers.

10. The module defined in claim 1 wherein said lamps are positioned in rows and are spaced apart from one another by substantially the same distance and has at least one hole of said multiplicity of cleaning fluid exit holes is located about half the distance between adjacent lamps.

11. The apparatus defined in claim 1 wherein said first header has a multiplicity of holes to receive said lamps and wherein each hole of said first header contains a threaded collar constructed to receive said lamps, o-rings positioned interiorly of said collars and nuts also constructed to receive said lamps and threaded around said collars and against said o-rings to seal said lamps to said first header in position.

12. The apparatus defined in claim 1 wherein said second header has a multiplicity of depressions to receive and maintain said lamps in position.

13. The apparatus defined in claim 1 wherein said second header has a multiplicity of openings to receive and maintain said lamps in position.

14. The apparatus defined in claim 13 further comprising a multiplicity of resilient, cup shaped grommets each positioned in each of said multiplicity openings of said second header to receive and maintain a corresponding lamp in position.

15. The apparatus defined in claim 14 wherein each of said grommets comprise:

a substantially cylindrically shaped body having an upper open end and a substantially test tube shaped closed lower end, at least a portion of said body being constructed to have an inner diameter substantially the same as or smaller than an outer diameter of said lamps; and a lip having a free end portion extending radially outwardly from said open end and having a groove extending along said free end portion thereof, said groove being constructed to about the thickness of a portion of said second header in which said multiplicity openings are located.

16. The apparatus defined in claim 15 wherein an inner diameter of a portion of said body proximate said lip is constructed larger than the outer diameter of said lamp, and said portion of said body proximate said lip has at least one hole or slit to permit fluids to flow from said second header and into said grommet and into contact with a corresponding lamp.

17. The module defined in claim 1 wherein said second header comprises a substantially hollow housing having a top plate, side walls and a floor.

18. The module defined in claim 17 wherein said floor is removable.

19. The module defined in claim 1 wherein said lamps are aligned substantially parallel with respect to one another and are oriented substantially perpendicular with respect to said headers.

20. The module defined in claim 1 wherein said first header comprises a substantially hollow housing having a top pan, side walls and a bottom plate.

21. The module defined in claim 20 wherein said top pan is removable.

22. The module defined in claim 1 wherein said first header contains at least one ballast connected to said lamps.

23. The module defined in claim 1 wherein said first header contains at least one electronic lamp controller connected to said lamps.

24. The module defined in claim 1 wherein said first header contains lamp monitoring means.

25. The module defined in claim 1 wherein said first header contains data collection means.

26. The module defined in claim 1 wherein said first header is provided with cooling means to dissipate heat into the surrounding atmosphere.

27. The module defined in claim 26 wherein said cooling means comprises a shroud surrounding at least a portion of said first header and a fan positioned interiorly of said shroud to circulate air through said shroud and into contact with said surrounded portion of said first header.

28. The module defined in claim 27 wherein said shroud surrounds three sides of said first header.

29. The module defined in claim 3 wherein each of said jackets has a substantially test tube shaped closed end and contains a resilient spacer positioned between said closed end and a corresponding lamp.

30. An immersible and portable module for irradiating fluids and capable of an in situ self cleaning comprising:

a multiplicity of ultraviolet light producing lamps;
a top header for receiving and maintaining in position said multiplicity of ultraviolet light producing lamps;
a bottom header located substantially vertically below said upper header for receiving and maintaining in position said multiplicity of lamps, said bottom header having a chamber with opening to receive cleaning fluids; and a hollow support member connected between said headers and passing said cleaning fluids therethrough;

said multiplicity of ultraviolet producing lamps being substantially aligned in parallel between said headers and connected to a power supply and controlling means;

said bottom header having a multiplicity of cleaning fluid exit holes in said chamber proximate said lamps to permit said cleaning fluids to flow through said opening into said chamber and outwardly from said holes and into contact with said lamps.

31. A fluid irradiation system comprising:

a channel through which fluids flow; and at least one immersible and in situ self cleaning module for irradiating said fluids comprising:

a multiplicity of ultraviolet light producing lamps;

a first header for receiving and maintaining in position said multiplicity of ultraviolet light producing lamps; and a second header for receiving and maintaining in position said multiplicity of lamps and having an opening to receive cleaning fluids, said multiplicity of lamps being positioned between said headers;

said second header having a multiplicity of cleaning fluid exit holes proximate said lamps to permit said cleaning fluids to flow into said opening and outwardly from said holes and into contact with said lamps.

* * * * *